(12) United States Patent
Ukegawa

(10) Patent No.: US 8,012,296 B2
(45) Date of Patent: Sep. 6, 2011

(54) PROCESS FOR MAKING DISPOSABLE WEARING ARTICLE

(75) Inventor: Kazuo Ukegawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 12/725,247

(22) Filed: Mar. 16, 2010

(65) Prior Publication Data

US 2010/0170615 A1   Jul. 8, 2010

Related U.S. Application Data

(63) Continuation of application No. 11/281,403, filed on Nov. 18, 2005, now Pat. No. 7,708,857.

(30) Foreign Application Priority Data

Nov. 19, 2004   (JP) .................................. 2004-336042

(51) Int. Cl.
| | |
|---|---|
| B29C 65/48 | (2006.01) |
| B29C 65/56 | (2006.01) |
| B32B 37/02 | (2006.01) |
| B32B 37/16 | (2006.01) |
| B32B 38/04 | (2006.01) |
| B32B 38/10 | (2006.01) |
| A61F 13/15 | (2006.01) |
| A61F 13/49 | (2006.01) |
| B29C 65/72 | (2006.01) |
| B32B 37/20 | (2006.01) |
| B32B 38/18 | (2006.01) |
| A61F 13/494 | (2006.01) |

(52) U.S. Cl. ......................... 156/269; 156/160; 156/302
(58) Field of Classification Search .................. 156/160, 156/269, 302
See application file for complete search history.

(56) References Cited

U.S. PATENT DOCUMENTS

| | | | |
|---|---|---|---|
| 5,766,737 | A | 6/1998 | Willey et al. |
| 6,264,643 | B1 | 7/2001 | Toyoda |
| 6,328,725 | B2 | 12/2001 | Fernfors |
| 6,432,248 | B1 | 8/2002 | Popp et al. |
| 6,830,153 | B2 | 12/2004 | French et al. |
| 7,189,301 | B2 | 3/2007 | Otsubo et al. |

(Continued)

FOREIGN PATENT DOCUMENTS

| | | |
|---|---|---|
| WO | 97/23180 | 7/1997 |
| WO | 01/87208 | 11/2001 |
| WO | 01/87209 A1 | 11/2001 |
| WO | 2004/016209 A1 | 2/2004 |
| WO | 2004/052258 | 6/2004 |

OTHER PUBLICATIONS

European Search Report for EP Application No. 05806959.2 mailed Jul. 6, 2009.

*Primary Examiner* — Sonya Mazumdar
(74) *Attorney, Agent, or Firm* — Lowe, Hauptman, Ham & Berner, LLP

(57) ABSTRACT

In a process for making disposable wearing article, a composite web running in a machine direction is formed with a pair of rectilinear slits extending in a cross direction and a notch intersecting these paired slits. A region surrounded by these slits and notch is cut away from the composite web to form a gap. In a step before the composite web is formed with the gap, second fastener means supported on a fastener base sheet strip are engaged with the associated pair of first fastener means previously bonded to the composite web opposed to each other about the gap as viewed in the machine direction and thereby the fastener base sheet strip is attached to the composite web so as to stride over the gap.

14 Claims, 9 Drawing Sheets

U.S. PATENT DOCUMENTS

| | | |
|---|---|---|
| 2001/0014798 A1 | 8/2001 | Fernfors |
| 2002/0148557 A1 | 10/2002 | Heller et al. |
| 2002/0174931 A1 | 11/2002 | Couillard et al. |
| 2004/0040642 A1 | 3/2004 | Otsubo et al. |
| 2004/0108043 A1 | 6/2004 | Otsubo |
| 2004/0112508 A1 | 6/2004 | Umebayashi et al. |
| 2004/0182502 A1 | 9/2004 | Wagner et al. |
| 2004/0194879 A1 | 10/2004 | Ohiro et al. |

PROCESS FOR MAKING DISPOSABLE WEARING ARTICLE

RELATED APPLICATIONS

The present application is a continuation of U.S. application Ser. No. 11/281,403 filed Nov. 18, 2005, and claims priority from Japanese Application Number 2004-336042 filed Nov. 19, 2004, the disclosures of which are hereby incorporated by reference herein in their entirety.

BACKGROUND OF THE INVENTION

The present invention relates to a process for making a disposable wearing article including fastener means.

There have already been proposed the pants-type wearing articles such as disposable pants-type diapers having front and rear waist regions detachably connected to each other along respective opposite lateral margins thereof by releasable and reusable fastener means. For example, WO 01/87209 A1 (hereinafter referred to as "REFERENCE") discloses a disposable training pants 500 and a process for making the same as illustrated in FIGS. 9 and 10 of the accompanying drawings. In the pants 500, opposite lateral margins of a front waist region 522 are provided on the inner surface thereof with first fastening means 582 and opposite lateral margins of a rear waist region 524 on the outer surface thereof with second fastening means 584 adapted to cooperate with the first fastening means 582. The first fastening means 582 may be formed, for example, by hook-type fasteners and the second fastening means 584 may be formed, for example, by loop-type fasteners. During the production process illustrated in FIG. 10, a continuous chassis 532 defining an outer configuration of the pants 500 runs from the left-hand side toward the right-hand side as viewed in FIG. 10. The front waist region 522 is provided on its inner surface with a front waist elastic member 554 attached thereto and the rear waist region 524 is provided on its inner surface with a rear waist elastic member 554 attached thereto. On both sides of a boundary line 592 defined between each pair of the adjacent pants 500, the first fastening means 582 are attached to these adjacent pants 500, respectively, and then the chassis 532 is partially cut away between these adjacent first fastening means 582, 582 to form a gap 579. These adjacent front waist regions 522, 522 are provided on the respective inner surfaces with the second fastening means 584 detachably attached to the respective first fastening means 582 so that the second fastening means 584 straddle the gap 579. While not illustrated, the chassis 532 is folded back on itself with the inner surface inside and then the inner surfaces of the respective rear waist regions 524 are bonded to the respective second fastening means 584. Thereafter the chassis 532 is cut along the respective boundary lines 592 to obtain the individual pants 500 as shown in FIG. 9.

Referring to FIG. 10, the continuous chassis 532 is conveyed by an endless belt from the left-hand side to the right-hand side. While the chassis 532 is kept in close contact with the endless belt under a vacuum suction effect, the respective front waist regions 522 arranged in a machine direction by the intermediary of the gaps 579 may be affected by a tensile force generated as this chassis 532 runs toward the right-hand side as viewed in FIG. 10 and thereby may jolt out of alignment or twist depending on the manner in which the chassis 532 is held in close contact with the endless belt. Consequentially, there is a possibility that the respective front waist regions 522 might be irregularly shaped in the continuously produced individual pants 500. Compared to the case in which the chassis 532 having none of the front elastic members 554 attached thereto, in the case of the chassis 532 having the front elastic members 554 having previously been attached thereto, the possibility that the respective front waist regions 522 might be irregularly shaped will become more actual due to contraction of the elastic members 554 affect the chassis 532.

SUMMARY OF THE INVENTION

The present invention aims to provide a process for making the disposable wearing article having front and rear waist regions thereof connected to each other along respective opposite lateral margins by the fastener means as in the case of the training pants described in the REFERENCE improved so that the continuously produced individual wearing articles can be regularly shaped even if a web as a basic material for the article is partially cut off to form gaps as the web runs in one direction.

The object set forth above is achieved, according to the present invention, by an improvement in the process for continuously making disposable wearing articles comprising the steps of feeding a web having an inner surface, an outer surface lying on the side opposite to the inner surface, and a pair of side edges extending in parallel to each other in a machine direction, folding the web in a cross direction orthogonal to the machine direction with a pair of the side edges falling in line, thereafter cutting the web successively along cutting line extending in the cross direction to form segments of the web each having a predetermined dimension in the machine direction, and detachably connecting each pair of adjacent boundary edges falling in line of the segments defined by the cutting line and extending in the cross direction in a vicinity of the side edges to output the individual wearing articles each having a waist-hole and a pair of leg-holes, successively side by side.

The improvement in such a process for making disposable wearing article according to the present invention comprises the steps as follows:

a) continuously feeding, in the machine direction, a first web having a first surface, a second surface lying on a side opposite to the first surface, first and second side edges extending in parallel to each other in the machine direction and a predetermined width in the cross direction;

b) continuously feeding, in the machine direction, a second web having a third surface, a fourth surface lying on a side opposite to third surface, a width larger than those of the first web, third and fourth side edges extending in parallel to each other in the machine direction, the third surface being opposed to the first surface and the first surface being placed upon and bonded to a middle zone of the third surface as viewed in the cross direction to form a composite web and then continuously feeding the composite web in the machine direction;

c) on the second surface of the first web or on the fourth surface of the second web in the composite web, forming first fastener means on both sides, as viewed in the machine direction, of a region to be formed with the cutting line so as to be interposed between the first and second side edges in the vicinity of the first side edge;

d) between the region to be formed with the cutting line and respective the first fastener means, forming said composite web with a pair of rectilinear slits extending in the cross direction beyond opposite ends of the first fastener means as viewed in the cross direction but extending neither to the third side edge nor the fourth side edge and opposed to each other about said region to be formed with the cutting line;

e) attaching a fastener base sheet strip extending in the machine direction so as to intersect the pair of rectilinear slits and having a pair of second fastener means thereon adapted to be detachably engaged with the first fastener means on both sides of the region to be formed with the cutting line to the composite web by putting the second fastener means into engagement with the first fastener means, respectively;

f) forming the composite web with notch intersecting the pair of rectilinear slits in a vicinity of the opposite ends of the first fastener means on the composite web;

g) cutting away a region surrounded by at least the pair of rectilinear slits and the notch from the composite web and then folding portions of the second web respectively extending in a vicinity of the third and fourth side edges along the first and second side edges, respectively, onto the second surface of the first web and bonding these portions to the second surface;

h) subsequently to the step g), folding the composite web in the cross direction with the first and second side edges thereof falling in line wherein one of the second surface of the first web and the fourth surface of the second web provided not with the first fastener lies inside;

i) in a vicinity of the second side edge, bonding the composite web folded in two to the fastener base sheet strip in a range defined between the region to be formed with the cutting line and the regions to be formed with the pair of rectilinear slits; and j) subsequently to the step i), cutting the composite web together with the fastener base sheet strip in the region to be formed with the cutting line.

According to the invention, the first web comprises a first sub-web and a second sub-web extending in parallel to each other in the machine direction, the first sub-web having a first outer side edge and a first inner side edge as viewed in the cross direction, the second sub-web having second outer side edge and second inner side edge also as viewed in the cross direction so that the first outer side edge and the second outer side edge form the first side edge and the second side edge of the first web, respectively, and the second web overlaps the first sub-web and the second sub-web so that the first and second inner side edges are connected with each other by an intermediary of the second web.

A first embodiment of the invention, further includes a step of attaching an assembly of body fluid absorbent materials as a body fluid absorbent member at least partially covered with a liquid-pervious sheet to the composite web.

A second embodiment of the invention, further includes a step of attaching a plurality of elastic members extending in the machine direction in stretched state between the first web and the second web along the first side edge.

According to a third embodiment of the invention, the second web is hydrophobic.

According to the invention, the second fastener means supported on the fastener base sheet strip are engaged with the associated first fastener means and thereby the fastener base sheet strip is attached to the composite web in the step preceding the step of cutting away the region surrounded by a pair of the rectilinear slits and the notch intersecting these paired slits from the composite web running in the machine direction. Such sequence of the steps is effective to eliminate a problem that the zones of the composite web lying along the first, second, third and fourth side edges might be significantly distorted and the continuously produced individual wearing articles might be irregularly shaped even if the composite web run under the tensile force functioning to pull the composite web in the machine direction. In addition, the composite web includes the second continuous sheet having a relatively enlarged width and therefore the slits extending beyond the opposite ends of the first fastener means may be formed even if the first fastener means are attached to the first continuous sheet in the vicinity of its first side edge and immediately adjacent the waist-hole's periphery.

The first embodiment of the invention allows the first sub-web and the second sub-web spaced from each other in the cross direction by a predetermined dimension and parallel running in the machine direction may be used in the place of the first web. By using these sub-webs, the front and rear waist regions of the wearing article can be easily made distinctive from each other with respect to various properties such as air-permeability, liquid-impermeability, strength, stretchability, color tone.

The second embodiment of the invention allows the wearing article to be provided with the body fluid absorbent pad.

According to the third embodiment, the elastic members extending in the machine direction may be attached to the first web as the principal component in the vicinity of the first side edge to make these elastic members serve as the waist elastic members in the wearing article.

According to the embodiment wherein the hydrophobic second web is used, the web may be folded back onto the inner surface of the first web to make the inner surface of the waist-hole periphery hydrophobic and thereby to eliminate a problem that the wetted periphery might undesirably cool the wearer's belly.

DETAILED DESCRIPTION OF THE PREFERRED EMBODIMENTS

Details of a process for making the disposable pants-type wearing article according to the present invention will be more fully understood from the description given hereunder with reference to the accompanying drawings.

Figure 1:
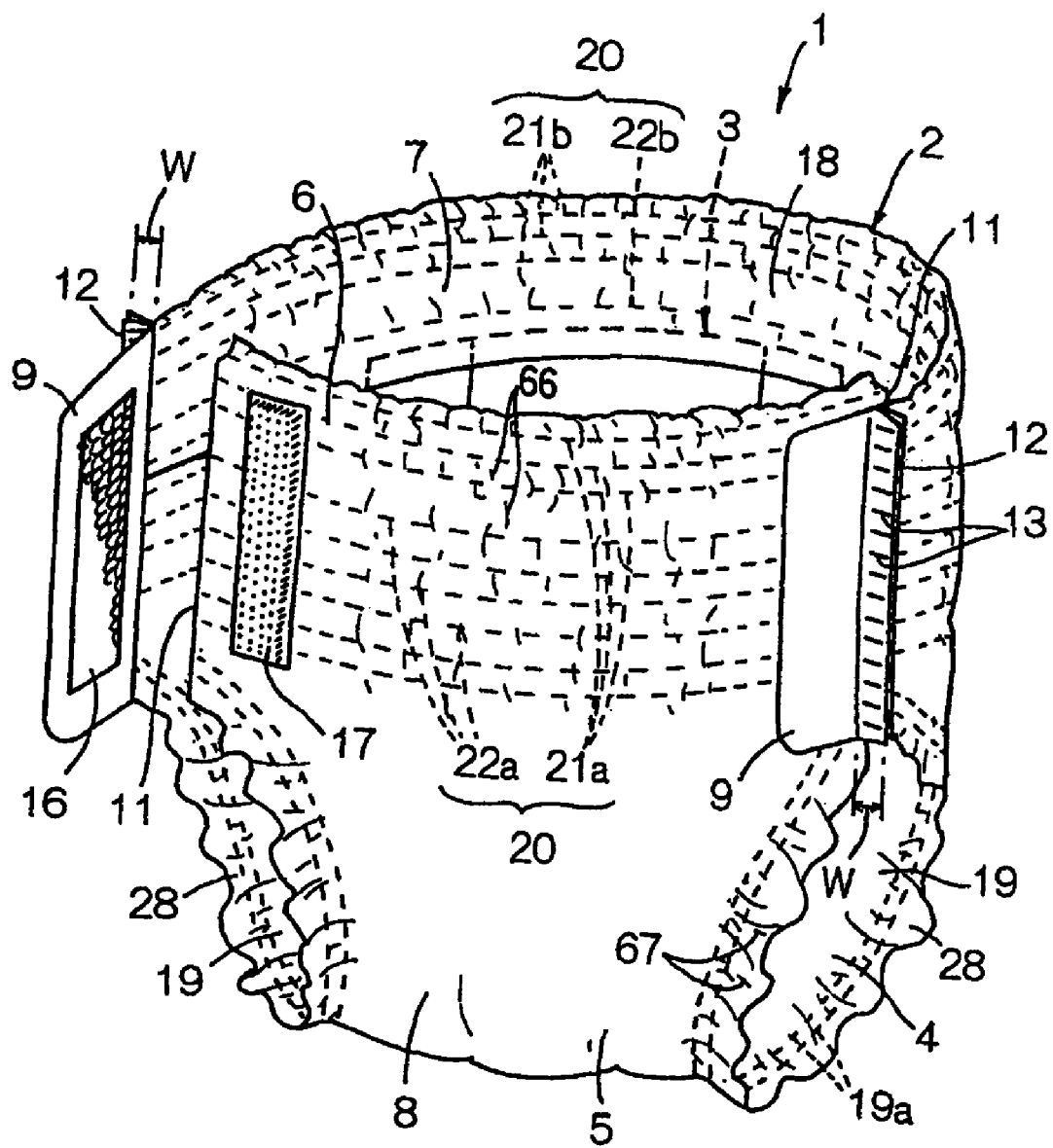
FIG. 1 is a perspective view showing a pants-type diaper.

A disposable wearing diaper 1 shown in FIG. 1 in a perspective view is made by a process according to the present invention and comprises a chassis 2 and a body fluid absorbent pad 3. The chassis 2 has a crotch region 8, a front waist region 6 extending forward from the crotch region 8 and a rear waist region 7 extending rearward from the crotch region 8. These regions 6, 7, 8 are formed from an outer sheet 5 facing a wearer's garment (not shown) and an inner sheet 4 lying on the inner side of the outer sheet 5 so as to face the wearer's body (not shown). The rear waist region 7 is provided, in the vicinity of transversely opposite side edges 12 thereof, with a pair of flaps 9 made of a sheet material prepared separately of the inner and outer sheets 4, 5 bonded to the region 7 by means of adhesive or sealing technique at a plurality of bonding spots 13 arranged intermittently in a vertical direction as viewed in FIG. 1. Each of the flaps 9 is provided on its inner surface with a loop member 16 of the mechanical fastener commonly known in the trade mark "Velcro" or the like attached thereto by means of adhesive or sealing technique. The front waist region 6 is provided on its outer surface, in the vicinity of opposite side edges 11, with hook members 17 of the mechanical fastener, respectively, attached thereto by means of adhesive or sealing technique. These loop members 16 and hook members 17 may be overlapped together to connect the front and rear waist regions 6, 7 with each other in the vicinity of the respective side edges 11, 12 of these waist regions 6, 7 in a detachable manner. It should be noted that, in FIG. 1, the front and rear waist regions 6, 7 are shown as being in connected state on the right-hand side and to be in a disconnected state on the left-hand side. First when the front and rear waist regions 6, 7 are connected with each other on both sides, the diaper 1 is formed with a waist-hole 18 and a pair of leg-holes 19. A waist elastic member 20 extends around the waist-hole 18 and a leg elastic member 19a extends around each of the leg-holes 19. So far as the illustrated embodiment is concerned, contraction of these elastic members 20, 19a causes the chassis 2 to form gathers 66, 67 undulating in a waist surrounding direction and leg surrounding direction, respectively.

Figure 2:
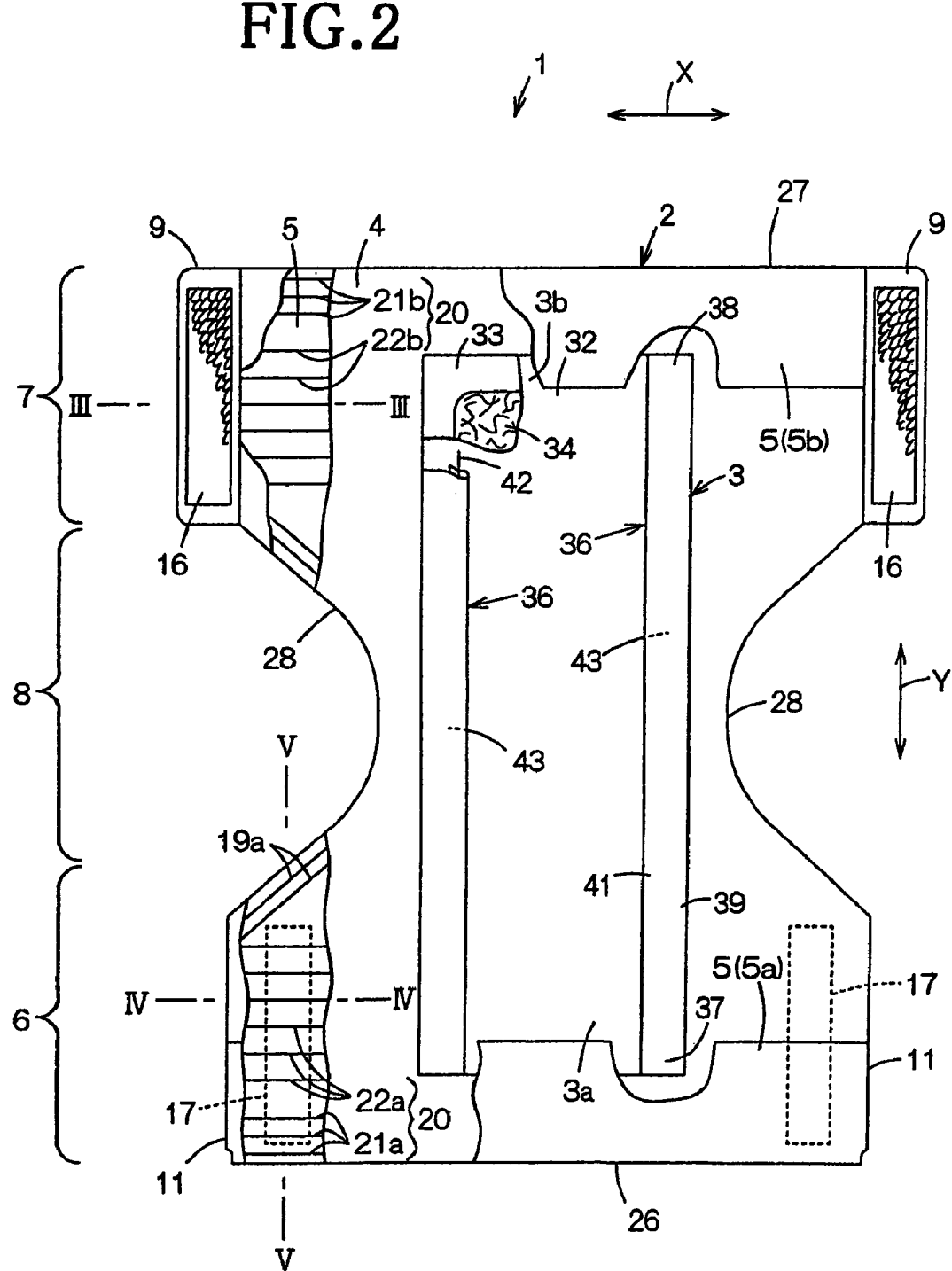
FIG. 2 is a developed and partially cutaway plan view showing the pants-type diaper.

FIG. 2 is a developed and partially cutaway plan view showing the diaper 1 of FIG. 1, in which the front waist region 6, rear waist region 7 and the crotch region 8 are flatly developed. More specifically, the front and rear waist regions 6, 7 are disconnected from each other while the leg elastic members 19a and the waist elastic member 20 are sufficiently stretched to make the gathers 66, 67 seen in FIG. 1 disappear. A transverse direction of the diaper 1 is indicated by a double-headed arrow X and a back-and-forth direction of the diaper 1 is indicated by a double-headed arrow Y being orthogonal to the double-headed arrow X. The double-headed arrow X corresponds also to a waist surrounding direction of the diaper 1. In the chassis 2, a dimension between the opposite side edges 11, 11 of the front waist region 6 is slightly smaller than a dimension between the opposite side edges 12, 12 and a difference between these two dimensions substantially corresponds to a dimension W over which the flaps 9 are attached to the rear waist region 7 as seen in FIG. 1. The front and rear waist regions 6, 7 respectively have front and rear ends 26, 27 both extending in the transverse direction X and opposite side edges 28 of the crotch region 8 describe circular arcs which are convex inwardly of the chassis 2. The waist elastic member 20 attached to the chassis 2 comprises at least single first elastic member 21a for the front waist region extending in a stretched state between the opposite side edges 11, 11 in the vicinity of the front end 26 and at least single first elastic member 21b for the rear waist region extending in a stretched state between the opposite side edges 12, 12 in the vicinity of the rear end 27. The waist elastic member 20 further comprises at least single second elastic member 22a for the front waist region extending in a stretched state between the opposite side edges 11, 11 and at least single second elastic member 22b for the rear waist region extending in a stretched state between the opposite side edges 12, 12 both lower than the first elastic members 21a, 21b and above the crotch region 8 as viewed in FIG. 1. Preferably, the first elastic members 21a, 21b respectively can tighten the wearer's waist more firmly than the second elastic members 22a, 22b respectively can. To achieve this, the elastic members having a tensile stress higher than that of the second elastic members 22a, 22b are used as the first elastic members 21a, 21b. The chassis 2 is further provided with the leg elastic members 19a attached in a stretched state thereto along the opposite edges 28 of the crotch region 8.

As shown in FIG. 2, the body fluid absorbent pad 3 comprises a liquid-pervious topsheet 32, a liquid-impervious backsheet 33 and a body fluid absorbent core 34 sandwiched between these two sheets 32, 33. The top- and backsheets 32, 33 extend beyond a peripheral edge of the core 34 so as to be overlapped and bonded together outside the peripheral edge of the core 34 by means of adhesive or sealing technique. The body fluid absorbent pad 3 is provided along opposite side edges thereof with a pair of leak-barrier cuffs 36 preferably made of a liquid-impervious sheet. Each of the leak-barrier cuffs 36 is bonded to the topsheet 32 at its longitudinally opposite ends 37, 38 and along its outer lateral edge 39 but left free from the topsheet 32 along its inner lateral edge 41. The inner lateral edge 41 is provided with an elastic member 42 extending in the back-and-forth direction Y and attached in a stretched state thereto. These leak-barrier cuffs 36 respectively form pockets 43 adapted to receive body fluids flowing in the transverse direction X. In the body fluid absorbent pad 3, the backsheet 33 is bonded to the inner sheet 4 of the chassis 2 by means of hot melt adhesive (not shown).

The outer sheet 5 has front and rear margins 5a, 5b folded back along the front and rear ends 26, 27, respectively, toward the inner sheet 4 so as to cover front and rear ends 3a, 3b of the body fluid absorbent pad 3, respectively, and bonded to the inner surface 4 as well as to the body fluid absorbent pad 3.

Figure 3:
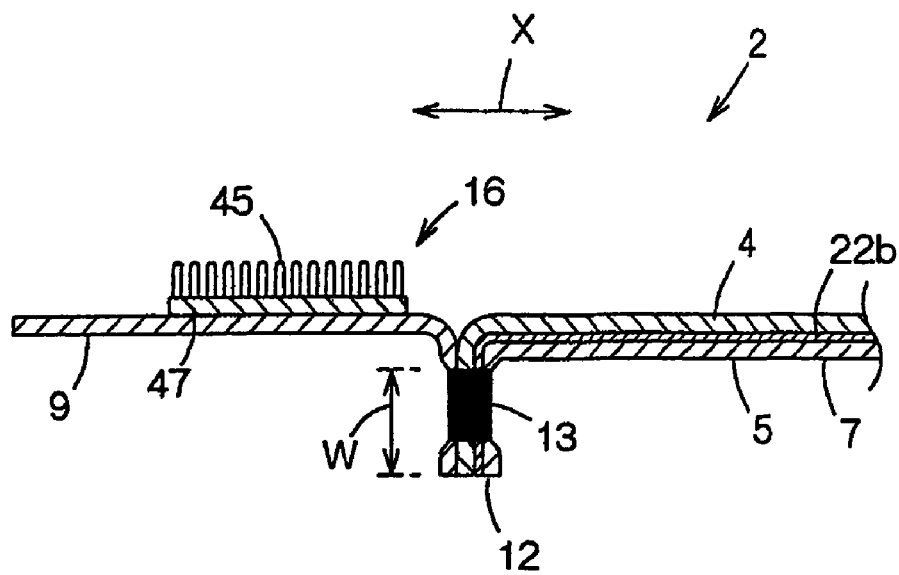
FIG. 3 is a sectional view taken along the line III-III in FIG. 2.

FIG. 3 is a sectional view taken along the line III-III in FIG. 2. The rear waist region 7 of the chassis 2 are overlapped in the vicinity of the opposite edges 12 thereof together with the respective flaps 9 and bonded to the respective flaps 9 at the bonding spots 13 arranged intermittently along the respective margins each having the dimension W. In the vicinity of the respective edges 12, the first and second elastic members 21b, 22b for the rear waist region are intermittently bonded to the inner and outer sheets 4, 5 by means of hot melt adhesive (not shown) and extend to the bonding spots 13. It should be noted that only the second elastic member 22b is seen in FIG. 3. The flaps 9 are bonded to the rear waist region 7 in the vicinity of the respective edges 12 thereof so firmly to ensure that the flaps 9 will never be peeled off from the rear waist region 7 even if the flaps 9 are pulled in the transverse direction X. Base sheets 47 defining the respective loop members 16 are bonded to the inner surfaces of the respective base sheets 47 and these base sheets 47 are formed on the respective inner surfaces thereof with a plurality of loops 45.

In such diaper 1, a nonwoven fabric or plastic film may be used as a stock material for the inner sheet 4 and the outer sheet 5. A nonwoven fabric or perforated plastic film may be used as a stock material for the topsheet 32 and a plastic film may be used as a stock material for the backsheet 33. Fluff pulp and/or super-absorbent polymer particles may be used as a stock material for the core 34. The inner sheet 4 and the outer sheet 5 are formed preferably from a hydrophobic sheet and more preferably by a liquid-impervious hydrophobic sheet.

Figure 4:
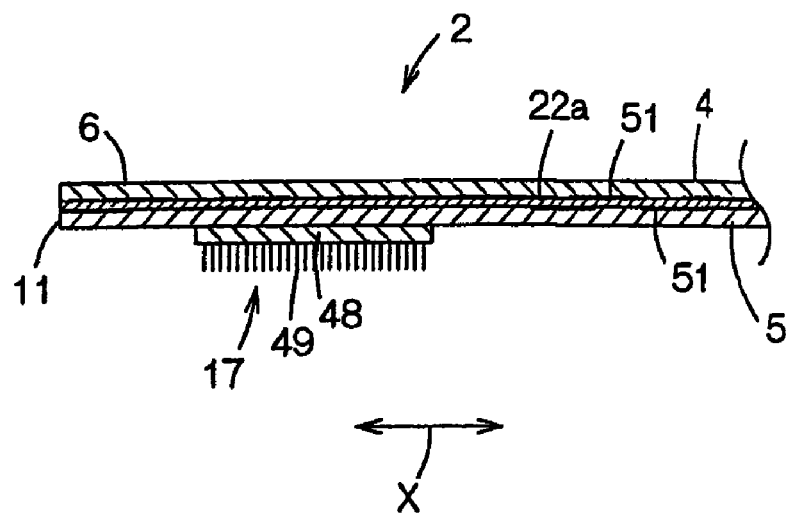
FIG. 4 is a sectional view taken along the line IV-IV in FIG. 2.
Figure 5:
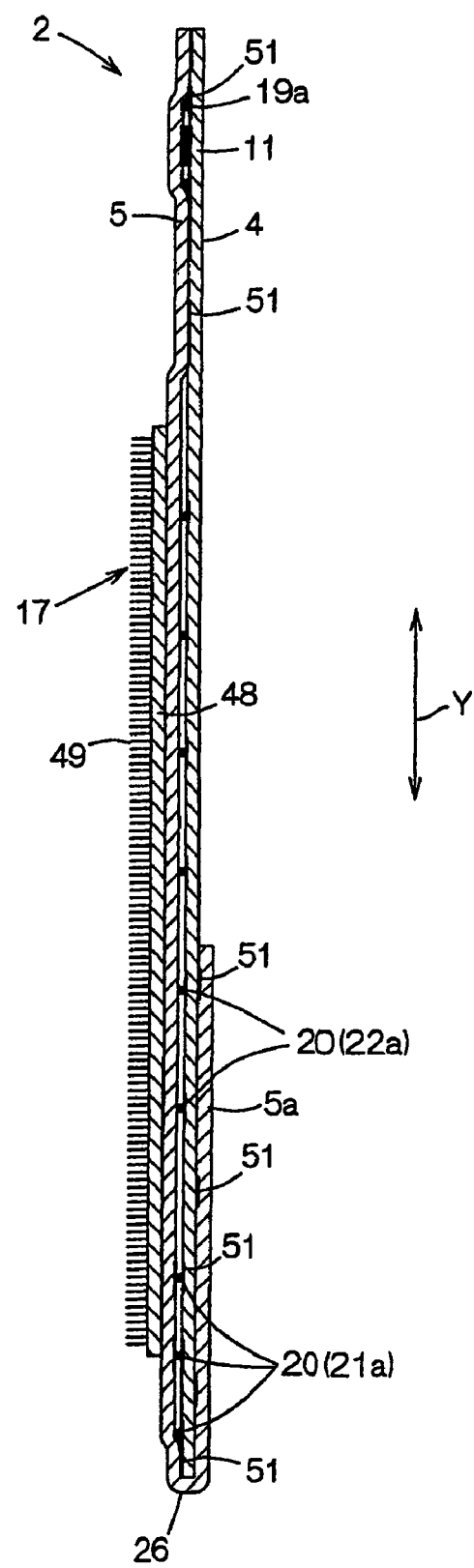
FIG. 5 is a sectional view taken along the line V-V in FIG. 2.

FIGS. 4 and 5 are sectional views taken along lines IV-IV and V-V, respectively, in FIG. 2. In the vicinity of the opposite side edges 11 of the front waist region 6 of the chassis 2, the respective hook members 17 comprise base sheets 48 bonded on the outer surface of the outer sheet 5 and a plurality of hooks 49 rising from the respective base sheets 48. Referring to FIG. 4, the chassis 2 has the inner sheet 4, the outer sheet and the second elastic member 22a are bonded one to another intermittently in the longitudinal direction of the second elastic member 22a by means of hot melt adhesive 51. Referring to FIG. 5, the outer sheet 5 is bonded to the first elastic member 21a, the leg elastic member 19a and the inner sheet 4 intermittently in the back-and-forth direction Y by means of hot melt adhesive 41. The front margin 5a of the outer sheet 5 is folded back along the front end 26 and bonded to the inner sheet 4 by means of hot melt adhesive 51.

Figure 6:
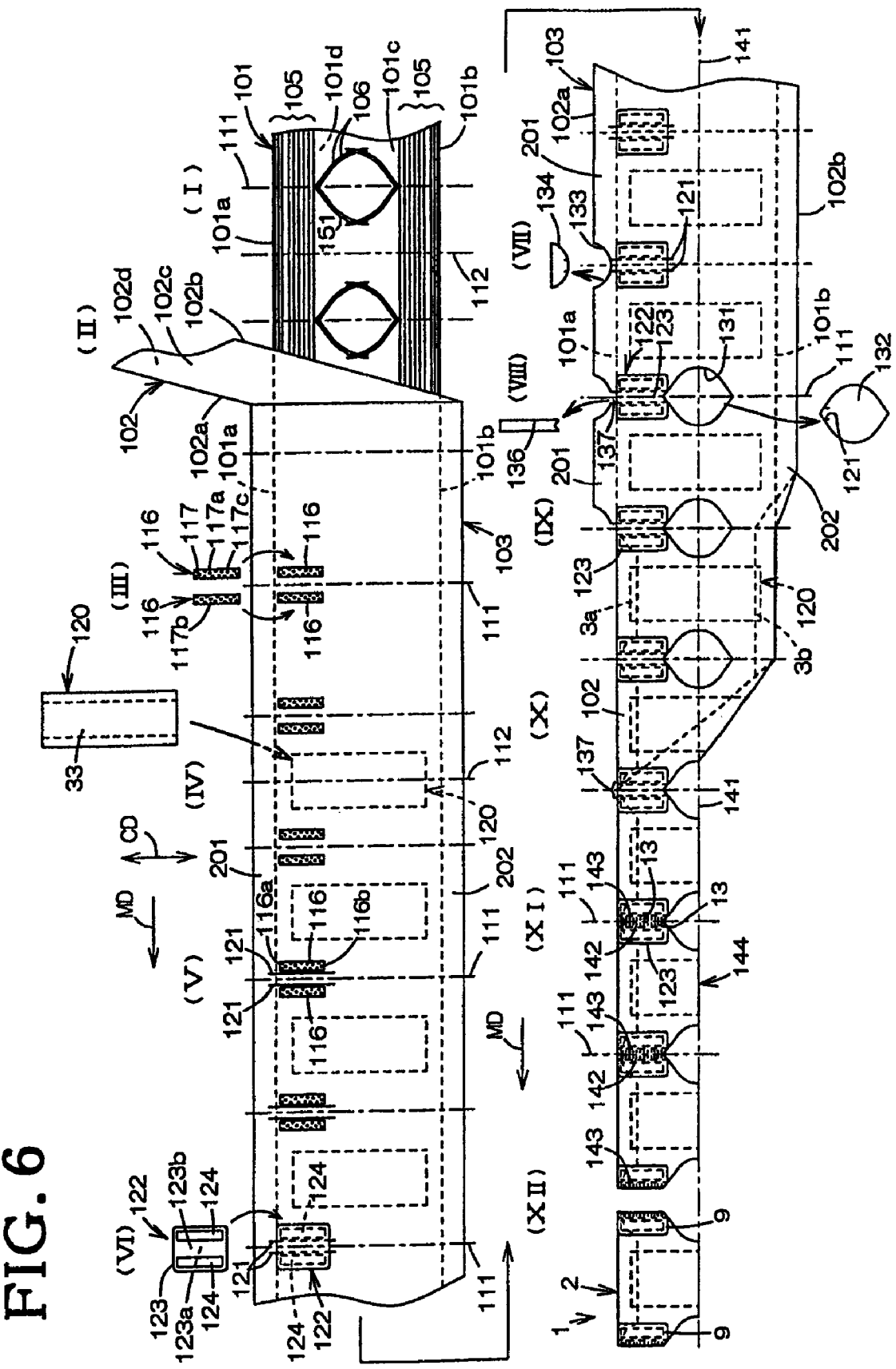
FIG. 6 is a diagram illustrating a part of a first embodiment of the process for making the pants-type diaper.

FIG. 6 is a diagram illustrating a part of a process for making the diaper 1 of FIG. 1, in which a machine direction and a cross direction being orthogonal to the machine direction are indicated by MD and CD, respectively, and a part of the process is illustrated in an enlarged scale. In a step I, a first continuous sheet 101 as a first web having a predetermined width runs in the machine direction MD. The first continuous sheet 101 has first and second side edges 101a, 101b extending in parallel to each other and extending in the machine direction MD, an upper surface 101c appearing in FIG. 6 and a lower surface 101d lying on the opposite side of the upper surface 101c. In the vicinity of the first and second side edges 101a, 101b, a plurality of continuous thread-like first elastic members 105 are attached in a stretched state to the upper surface 101c of the first continuous sheet 101. In intermediate region between the first and second side edges 101a, 101b as viewed in the cross direction CD, a plurality of thread-like second elastic members 106 forming an annulus 151 are attached in a stretched state to the upper surface 101c of the first continuous sheet 101. These annuli 151 are formed on the first sheet 101 at regular intervals intermittently in the machine direction MD.

In a step II, a second continuous sheet 102 as a second web which has a width larger than that of the first continuous sheet 101 as the first web, first and second side edges 102a, 102b, an upper surface 102c and a lower surface 102d lying on the side opposite to the upper surface 102c is continuously fed in the machine direction MD with the upper surface 102 facing upward so that a middle region of the lower surface 102d as viewed in the cross direction may be placed on and bonded to the upper surface 101c of the first continuous sheet 101 and thereby a first composite sheet 103 as a composite web may be formed. Preferably, these lower surface 102d and upper surface 101c are bonded to each other in the machine direction MD as well as in the cross direction CD. In the composite sheet 103, regions 201, 202 defined along the first and second side edges 102a, 102b of the second continuous sheet 102 lie outside the first and second side edges 101a, 101b of the first continuous sheet 101. In FIG. 6, an imaginary line 111 extending across the first continuous sheet 101 and the first composite sheet 103 is a first center line bisecting each of the annuli 151 in the machine direction and an imaginary line 112 extending across the first continuous sheet 101 and the first composite sheet 103 is a second center line bisecting a distance between each pair of the adjacent annuli 151, 151. The first center line 111 defines a cutting line in a step XII as will be described later.

In a step III, a pair of the hook members 116 are attached to the upper surface 102c of the second continuous sheet 102 making the part of the first composite sheet 103 in a region extending in the vicinities of the first center line 111 and the first side edge 101a so as to be laid symmetrically about the first center line 111. Each of the hook members 116 destined to form the hook member 17 in FIGS. 1 and 4 comprises a first base sheet 117 and hooks 117c rising on an upper surface 117a of the first base sheet 117. The hook member 117 has a lower surface 117b opposite to the upper surface 117a attached to the second continuous sheet 102. These first base sheet 117 and hooks 117a are destined to form the base sheet 48 and the hooks 49 in FIG. 4.

In a step IV, a body fluid absorbent member 120 is attached to the lower surface 101d of the first continuous sheet 101 making the part of the first composite sheet 103 by means of hot melt adhesive (not shown) with transverse center line (not shown) of the body fluid absorbent member 120 falling on the second center line 112. The body fluid absorbent member 120 is destined to form the body fluid absorbent pad 3 in FIG. 2 and shown in FIG. 6 as viewed from the side of the backsheet 33.

In a step V, the first composite sheet 103 is formed between the first center line 111 and the respective hook members 116 with rectilinear slits 121 passing completely through the first composite sheet 103 and extending in the cross direction CD. The slits 121 extend beyond upper and lower ends 116a, 116b of the hook members 116 as viewed in the cross direction CD and is illustrated herein as extending beyond the first side edge 101a of the first continuous sheet 101. It should be noted that the slits 121 extend neither to the second side edge 101b of the first continuous sheet 101 nor to the first side edge 102a of the second continuous sheet 102.

In a step VI, a loop member 122 strides across the first center line 111 and is detachably attached to a pair of the adjacent hook members 116. The loop member 122 comprises a base sheet 123 having upper and lower surfaces 123a, 123b and a pair of loop zones 124 formed on the lower surface 123b of the base sheet 123. In FIG. 6, the lower surface 123b of the base sheet 123 is illustrated to face the viewer of FIG. 6. These paired loop zones 124 are spaced from each other in the machine direction MD by substantially the same dimension as the dimension by which the paired hook members 116 cooperating with those paired loop zones 124. Each of the loop zones 124 has dimensions substantially the same as or slightly larger than those in each of the hook members 116 cooperating with this loop zone 124 in the machine direction MD as well as in the cross direction CD. The base sheet 123 is made of a strip of nonwoven fabric or plastic film having sufficient dimensions in the machine direction MD as well as in the cross direction CD to form these paired loop zones 124. The loop member 122 as illustrated is turned over so that the loop zones 124 face the hook members 116 and then attached to the hook members 116.

In a step VII, the side edge 201 of the second continuous sheet 102 making the part of the first composite sheet 103 is formed with a generally arc notch 133. The arc notch 133 has its open ends intersecting with the first side edge 102a of the second continuous sheet 102 and its closed end intersecting the paired slits 121. Along this notch 133, an arc notch piece 134 is cut away from the first composite sheet 103.

In a step VIII, an annular notch 131 which strides across the first center line 111 and is symmetric about the first center line 111. The annular notch 131 is formed so as to intersect respective ends of the paired slits 121 opposed to each other about the first center line 111 which extend aside toward the second side edge 102b. A generally oval-shaped piece 132 defined inside the annular notch 131 is cut away from the first composite sheet 103 and an elongate piece 136 surrounded by the paired slits 121, the annular notch 131 and the generally arc notch 133 is also cut away to form the first composite sheet 103 with a gap 137. It should be understood here that, through this gap 137, the base sheet 123 for the loop members 122 having previously been bonded to the first composite sheet 103 is exposed.

In a step IX, the side edge 201 of the second continuous sheet 102 extending outside the first side edge 101a of the first continuous sheet 101 and the side edge 202 of the second continuous sheet 102 extending outside the second side edge 101b of the first continuous sheet 101 are folded back along these first side edges 101a and the second side edge 101b toward the lower surface 101d of the first continuous sheet 101. The side edges 201, 202 are bonded to the lower surface 101d of the first continuous sheet 101 by means of hot melt adhesive (not shown). The preferred dimensions of the side edges 201, 202 as measured in the cross direction CD are sufficiently large to cover the ends of the body fluid absorbent member 120 having previously been attached to the lower surface 101d, i.e., the ends 3a, 3b in FIG. 2. These side edges 201, 202 are bonded also to the ends 3a, 3b to form the front and rear ends 5a, 5b of the outer sheet 5 in the diaper 1 shown in FIG. 2.

In a step X, the first composite sheet 103 is folded along a third center line 141 bisecting the width of the first continuous sheet 101 with the first continuous sheet 101 inside and with the first and second side edges 101a, 101b put flat together.

In a step XI, the first continuous sheet 101 and the base sheet 123 for the loop members 122 are opposed to each other in the gap 137, so first and second bonding regions 142, 143 extending in the cross direction CD on both sides of the first center line 111 as viewed in the machine direction MD are formed in which the first continuous sheet 101 and the base sheet 123 are bonded to each other. The first composite sheet 103 having been processed in this manner will be referred to as a second composite sheet 144 in subsequent steps. In the second composite sheet 144, the first and second bonding regions 142, 143 are substantially similar to each other with respect to an arrangement thereof except that the first bonding region 142 lies in front of the first center line 111 in the machine direction MD and the second bonding region 143 lies behind the first center line 111 in the machine direction MD. These first and second bonding regions 142, 143 are respectively illustrated as aggregates of the bonding spots 13 (See FIG. 1) arranged intermittently in the cross direction CD.

In a step XII, the second composite sheet 144 and the base sheets 123 are cut along the cutting lines defined by the first center lines 111 to obtain the individual pants-type diapers 1 output successively side by side in the machine direction MD.

The diaper 1 obtained by these steps I through XII is identical to the diaper 1 shown in FIG. 1. The first and second continuous sheets 101, 102 are cut in the step XII into the individual inner sheet 4 and the individual outer sheet 5 of the diaper 1 shown in FIG. 1. The body fluid absorbent member 120 of FIG. 6 is destined to form the body fluid absorbent pad 3 of FIG. 1. The first composite sheet 103 lying above the third center line 141 is destined to form the rear waist region 6 and apart of the crotch region 8. The hook members 116 are destined to form the hook members 17, the base sheet 123 of the loop members 122 are cut along the first center line 111 to form each pair of the flaps 9 on both sides of this first center line 111, and the loop members 124 are destined to form the loop members 16 of FIG. 1. The flaps 9 are attached to the rear waist region 7 at the bonding spots 13 in the first and second bonding regions 142, 143. In the diaper 1 of FIG. 1, the opposite side edges 11 of the front waist region 6 are defined by the slits 121 in the first composite sheet 103, and the opposite side edges 12 in FIG. 1 are formed by cutting the second composite sheet 144 along the first center lines 111, wherein the side edges 11 and the vicinity thereof are detachably connected with the side edges 12 and the vicinity thereof through the intermediary of the respective flaps 9. The annular notch 131 formed on the first composite sheet 103 is destined to form the opposite side edges 28 of the crotch region 8. While a plurality of the first elastic members 105 are destined to for the elastic members 21a, 21b and 22a, 22b, both the number of these elastic members 105 and the dimension by which these elastic members 105 are spaced one from another in the cross direction CD are not specified. While the second elastic members 106 are destined to form the leg elastic members 19a, both the number of these elastic members 106 and the shape of the annulus 51 formed by these elastic members 105 are also not specified. Compared to the diaper 1 of FIG. 1 in which one of the paired flaps 9 is connected to the front waist region 6 and the other is left free from the front waist region 6, the diaper 1 of FIG. 6 has the both flaps 9 are connected to the front waist region 6.

During the process illustrated in FIG. 6, a tensile force in the machine direction MD acts upon the first composite sheet 103 running in the machine direction MD. However, in the step VIII for forming the first composite sheet 103 with the gaps 137, the base sheet 123 of the loop member 122 has previously been attached to the first composite sheet 103 in such a manner that the base sheet 123 extends in the machine direction MD to stride across the gap 137. In addition, the side edge 201 of the second continuous sheet 102 remains continuous in the machine direction MD even after the gap 137 has been formed. During the process illustrated in FIG. 6, the tensile force acting upon the first composite sheet 103 so as to drive this in the machine direction MD is not affected by the presence of the gap 137. In other words, the tensile force can act uniformly on the extent of the first composite sheet 103 beyond the gap 137 (i.e., the right-hand side of FIG. 6) along the first side edge 102a of the second continuous sheet 102 and the first side edge 101a of the first continuous sheet 101. The base sheet 123 attached to the first composite sheet 103 so as to stride across the gap 137 effectively restraints contraction of the elastic members 105. With such an arrangement, it is ensured that the tensile force uniformly acts on the first composite sheet 103 along the first and second side edges 101a, 101b of the first continuous sheet 101. Consequently, it is not apprehended that the front and rear waist regions 6, 7 might have shapes distorted. It is also not apprehended that the front and rear waist regions 6, 7 of the continuously produced individual diapers 1 might have irregular shapes. The slit 121 extends beyond the opposite ends 116a, 116b of the hook member 116 and, when the end 116a of these opposite ends 116a, 116b lies closely adjacent to the first side edge 101a of the first continuous sheet 101, the slit 121 may extend beyond the first side edge 101a to the side edge 201 of the second continuous sheet 102 as in the embodiment illustrated.

The step of forming the arc notch 133 and the step of forming the annular notch 131 may be sequentially reversed in the process illustrated in FIG. 6. It is also possible to attach the body fluid absorbent member 120 to the first composite sheet 103 in the other step than the step IV.

Figure 7:
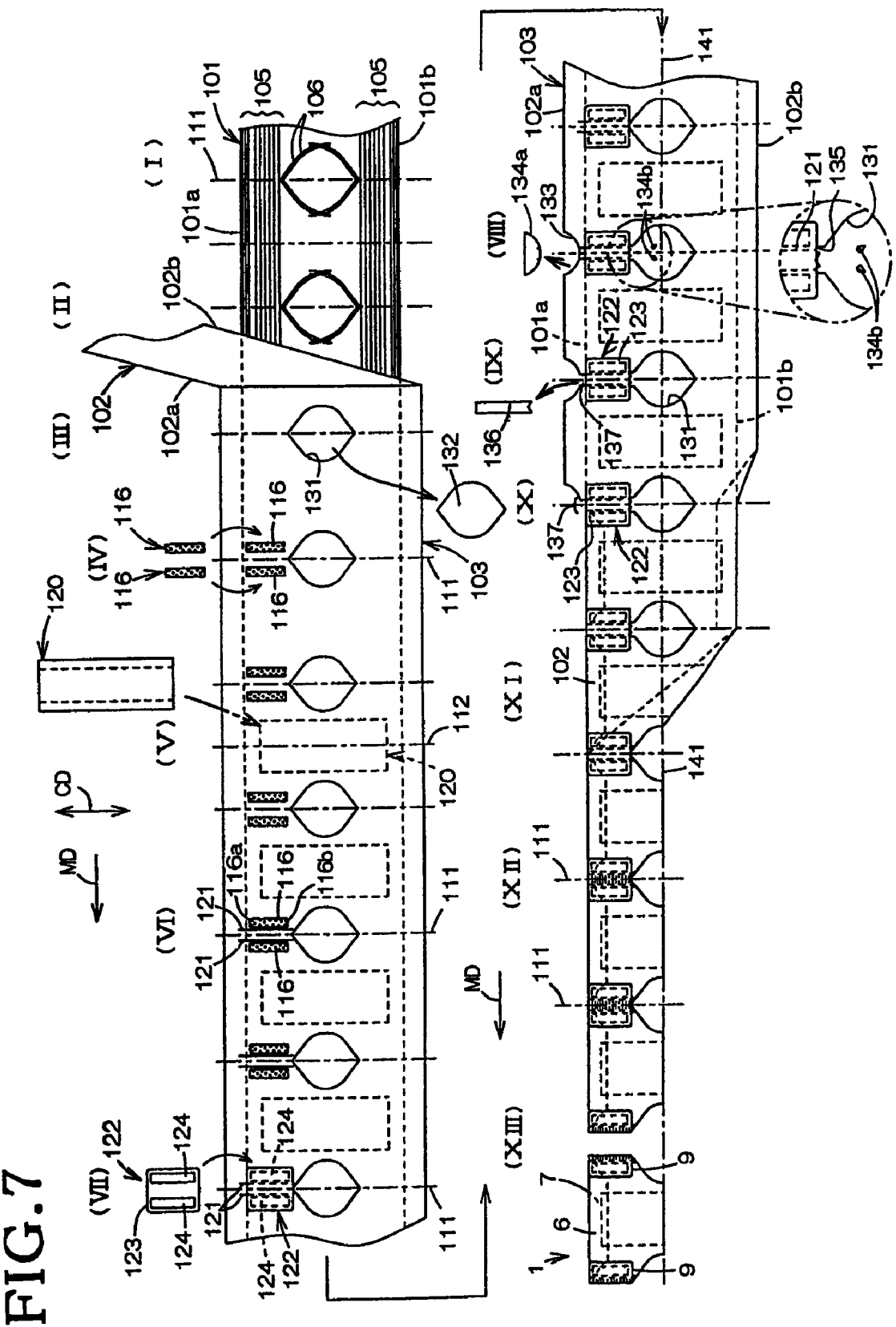
FIG. 7 is a diagram similar to FIG. 6, illustrating a second embodiment of the process for making the pants-type diaper according to the invention.

FIG. 7 is a diagram similar to FIG. 6, illustrating one preferred embodiment of the process for making the pants-type diaper according to the invention. In this embodiment, the first continuous sheet 101 and the second continuous sheet 102 are bonded to each other in the step II to form the first composite sheet 103 and, in the step III, the annular notch 131 which is symmetric about the first center line 111 and the generally oval-shaped piece 132 is cut away from the first composite sheet 103.

In the step IV, the hook member 116 is attached to the first composite sheet 103 as in the step III of the process illustrated in FIG. 6.

In the step V, the body fluid absorbent member 120 is attached thereto on the second center line 112 as in the step IV of the process illustrated in FIG. 6.

In the step VI, the slits 121 are formed on both sides of the first center line 111 as in the step V of the process illustrated in FIG. 6. Each of the slits 121 extends in the cross direction CD beyond the opposite ends 116a, 116b of the hook member 116 but extends neither to the first side edge 102a of the second continuous sheet 102 in the first composite sheet 103 nor to the annular notch 131.

In the step VII, a pair of loop zones 124 of the loop member 122 are detachably engaged with the hook members 116 laid on both sides of the first center line 111 as in the step VI of the process illustrated in FIG. 6.

In the steps VIII and IX, the arc notch 133 intersecting the ends of the slits 121 is formed as in the steps VII and VIII of the process illustrated in FIG. 6 and, in addition, a pair of inverted arc notches 135 is formed as generally second U-shaped notches. These inverted arc notches 135 respectively have bottoms intersecting the lower ends of the slits 121 and tops intersecting the annular notch 131. An arc notch piece 134a and a pair of inverted arc notch pieces 134b are cut away from the first composite sheet 103 and an elongate piece 136 surrounded by the arc notch 133, a pair of the slits 121, the annular notch 131 and a pair of the inverted arc notches 135 is cut away from the first composite sheet 103. The first composite sheet 103 is formed with the gap 137 as the elongate piece 136 is cut away from the first composite sheet 103. Through this gap 137, the base sheet 123 of the loop member 122 is exposed. The inverted arc notches 135 and the other details are encircled in FIG. 7 and illustrated in an enlarged scale.

The step X and the subsequent steps correspond to the step IX in the process illustrated in FIG. 6.

The process illustrated in FIG. 7 is different from the process illustrated in FIG. 6 in that the first composite sheet 103 is formed with the rectilinear slit 121 after formation of the annular notch 131. In the process illustrated in FIG. 7 also, the regions extending along its first and second side edges 102a, 102b of the second continuous sheet 102 as well as the regions extending along its first and second side edges 101a, 101b of the first continuous sheet 101 are uniformly subjected to the tensile force as in the process illustrated in FIG. 6. Consequentially, there is no anxiety that the respective front and rear waist regions 6, 7 of the individual diapers 1 produced by the process illustrated in FIG. 7 might be significantly distorted and irregularly shaped.

Figure 8:
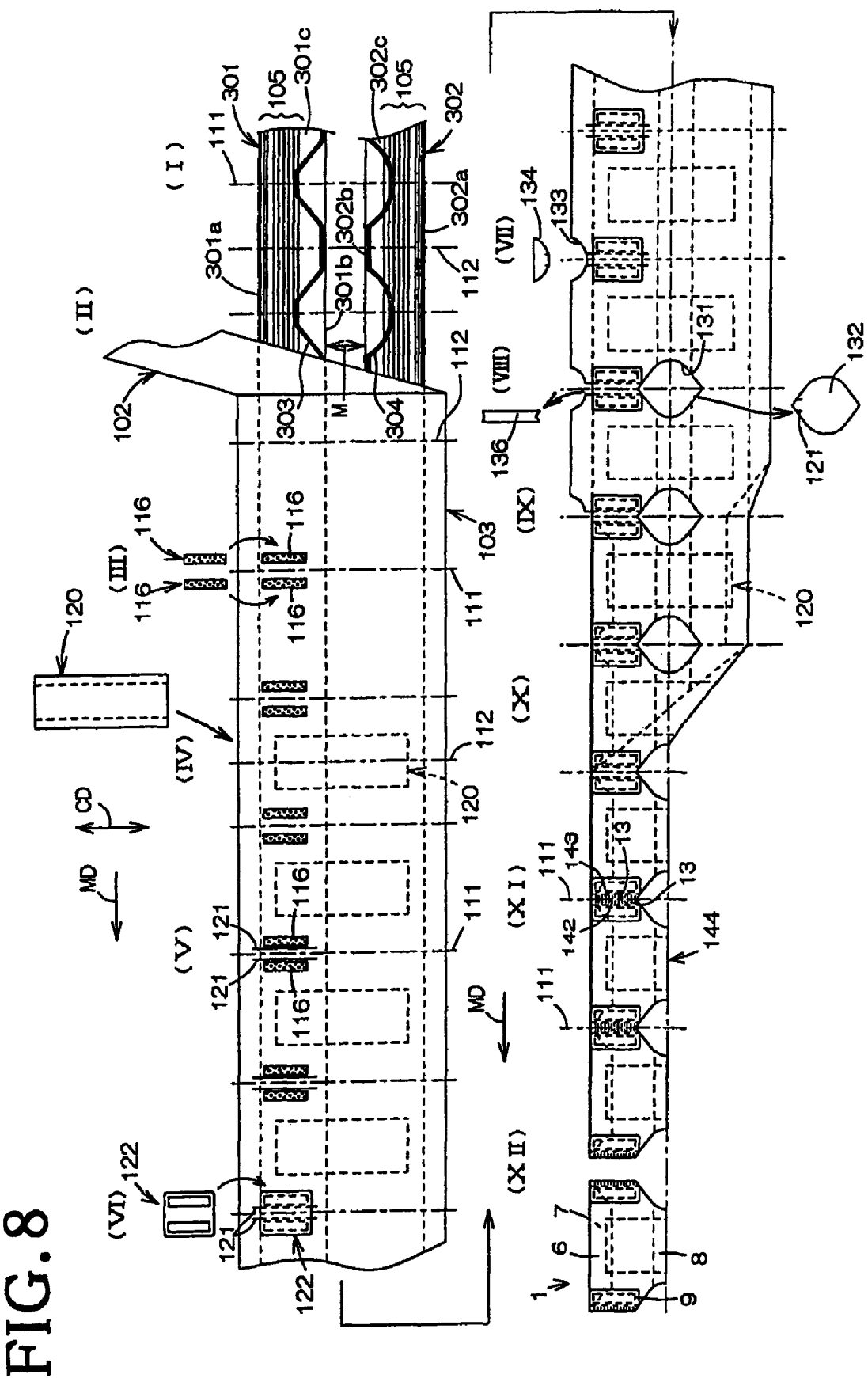
FIG. 8 is a diagram similar to FIG. 6, illustrating a third embodiment of the process for making the pants-type diaper according to the invention.
Figure 9:
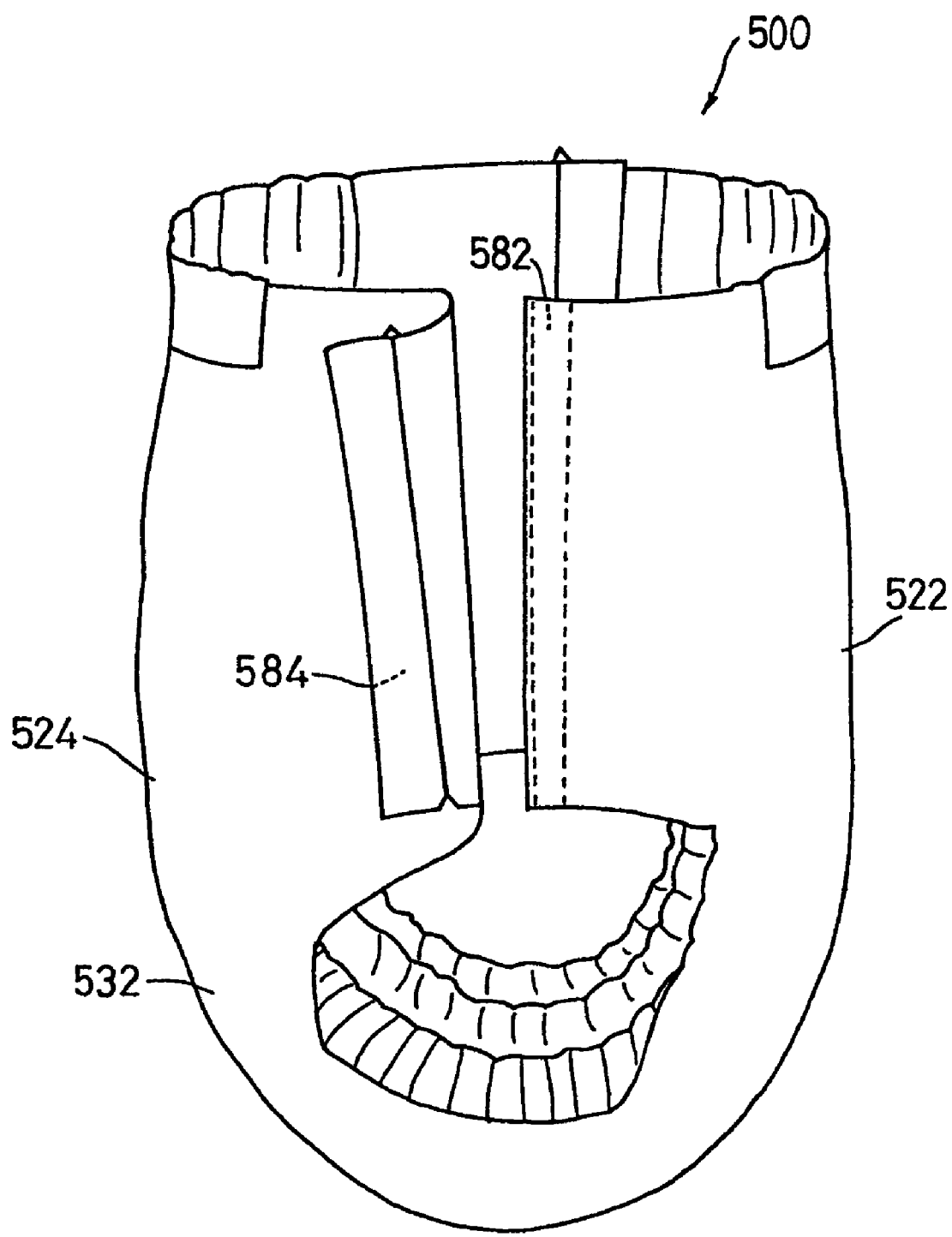
FIG. 9 is a perspective view showing an example of the conventional pants-type wearing article.
Figure 10:
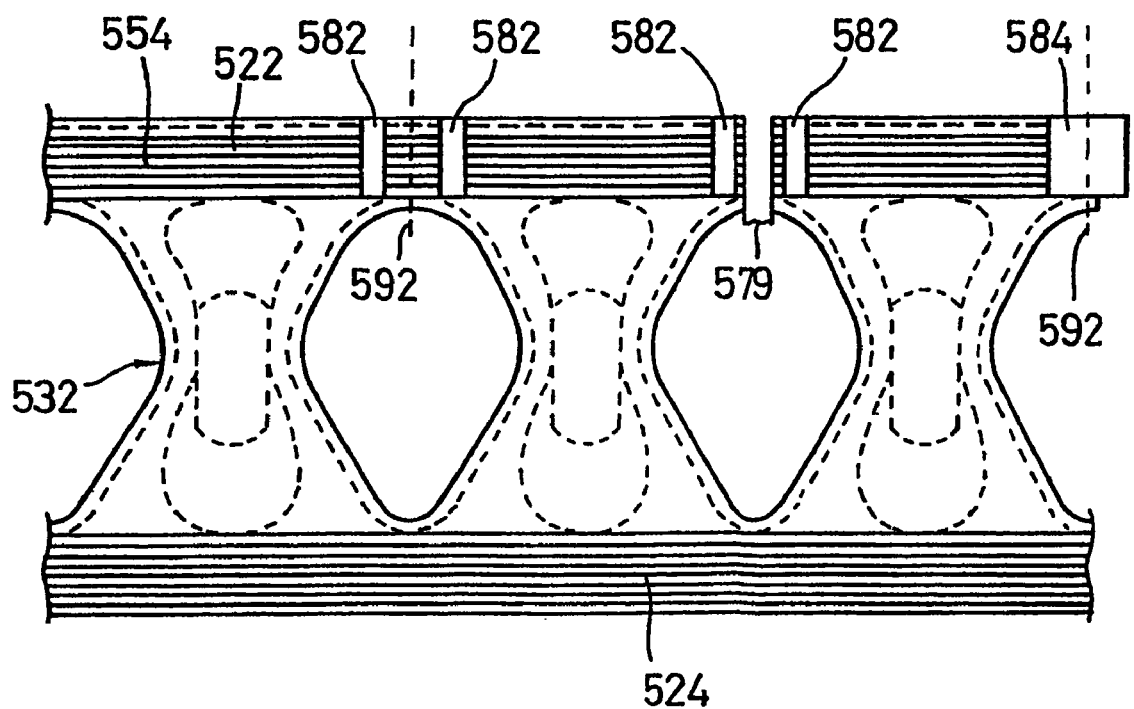
FIG. 10 is a diagram illustrating the process for making the pants-type diaper of FIG. 9.

FIG. 8 is a diagram similar to FIG. 6, illustrating a third embodiment of the process for making the pants-type diaper according to the invention. In this process, the first continuous sheet 101 used in the process illustrated in FIG. 6 is replaced by first continuous sub-sheet 301 and second continuous sub-sheet 302 both running in the machine direction MD. The first continuous sub-sheet 301 has first outer side edge 301a and first inner side edge 301b extending in parallel to each other in the machine direction MD and the second continuous sub-sheet 302 has a second outer side edge 302a and a second inner side edge 302b extending in parallel to each other in the machine direction MD. The first inner side edge 301b and the second inner side edge 302b are spaced from each other in the cross direction CD by a distance M. The first outer side edge 301a and the second outer side edge 302a are regions corresponding to the first side edge 101a and the second side edge 101b of the first continuous sheet 101 in FIG. 6 and a dimension between the first outer side edge 301a and the second outer side edge 302a corresponds to the width of the first continuous sheet 101. The first and second continuous sub-sheets 301, 302 are provided on respective upper surfaces 301c, 302c with a plurality of thread-like first elastic members 105 stretched in the machine direction and attached in such a stretched state thereto. These upper surfaces 301c, 302c are additionally provided between each pair of the adjacent second center lines 112 with a plurality of thread-like third and fourth elastic members 303, 304 each describing a curve symmetrically about the first center line 111 attached in stretched state thereto, respectively. The first elastic members 105 correspond to the first elastic members 105 in FIG. 6. The third and fourth elastic members 303, 304 replace the second elastic members 106 in FIG. 6 and cooperate together in the diaper 1 to tighten the diaper 1 in the vicinity of its leg-holes closely around the wearer's legs.

The steps I through XII of the process illustrated in FIG. 8 are substantially the same as the steps I through XII except that the second continuous sheet 102 and the body fluid absorbent member 120 are overlapped on and bonded to the first and second sub-sheets 301, 302 so that these sub-sheets 301, 302 are connected to each other by the intermediary of the second continuous sheet 102 and the body fluid absorbent member 120. In the diaper 1, the first continuous sub-sheet 301 cooperates with the second continuous sheet 102 to form the front waist region 6 while the second continuous sub-sheet 302 cooperates with the second continuous sheet 102 to form the rear waist region 7. The crotch region 8 of the diaper 1 is formed from the second continuous sheet 102 and the body fluid absorbent member 120. The first and second continuous sub-sheets 301, 302 may be formed from materials which are different from each other with respect to various properties such as liquid-impermeability, strength, stretchability and color tone to provide the front and rear waist regions 6, 7 of the diaper 1 with distinctive properties, respectively.

In the embodiment illustrated in FIG. 6, the width of the second continuous sheet 102 is larger than the width of the first continuous sheet 101 and, in the embodiment illustrated in FIG. 8, the width of the second continuous sheet 102 is larger than the width between the respective outer side edges 301a, 302a of the first and second continuous sub-sheets 301, 302 replacing the first continuous sheet 101. However, the present invention may be exploited also with the second continuous sheet 102 having a width smaller than a width of the first continuous sheet 101 or with the second continuous sheet 102 having a width smaller than a width between the respective outer side edges 301a, 302a of the first continuous sub-sheet 301 and the second continuous sub-sheet 302. In FIG. 6, for example, when the first continuous sheet 101 has a width larger than a width of the second continuous sheet 102, the first continuous sheet 101 may be folded back along the first and second side edges 102a, 102b of the second continuous sheet 102 and bonded to the upper surface 102c of the second continuous sheet 102 so that these first and second side edges 102c, 102b may form the front end 36 and the rear end 37 of the diaper 1, respectively. In this case, the hook members 116 and the loop members 122 may be attached to the lower surface 101d of the first continuous sheet 101 while the body fluid absorbent member 122 may be attached to the upper surface 102c of the second continuous sheet 102 to which none of the hook members 116 is attached.

The present invention may be exploited using neither the first elastic members 105 nor the second elastic members 106 both having been used in the embodiments illustrated in FIGS. 6 and 7. Alternatively, the elastic members 105 laid aside toward the first side edge 101a of the first continuous sheet 101 may be different from the elastic members 105 laid aside toward the second side edge 101b with respect to the number of the elastic members as well as the stretch stress. The annular notch 131 shaped to be substantially in symmetric relationship about the third center line 141 may be replaced by an annular notch 131 shaped asymmetrically about the third center line 141. It is also possible without departing from the scope of the invention to attach the hook members 17 to the rear waist region 7 and to attach the loop members 16 to flaps extending from the front waist region 6 toward the rear waist region 7 so that these hook and loop members 17, 16 may be detachably engaged one with another in the rear waist region 7 rather than in the front waist region 6. In other words, it is selectively possible without departing from the scope of the invention to form the front waist region 6 or the rear waist region 7 by using the region of the first composite sheet 103 extending above the third center line 141 as viewed in FIGS. 6 and 7. It is also possible to replace the loop members 16 in the illustrated embodiments by the hook members and to replace the hook members 17 by the loop members. Furthermore, the fastener means used in the present invention to connect the front and rear waist regions 6, 7 with each other are not limited to the mechanical fastener consisting of the loop member 16 and the hook member 17. The invention may be exploited further alternative manner. For example, one of the loop member 16 and the hook member 17 may be replaced by a pressure-sensitive adhesive layer formed by coating one of the front waist region 6 and the rear waist region 7, or the flaps 9 with a pressure-sensitive adhesive and the other of loop member 16 and the hook member 17 may be replaced by target zone(s) on which the pressure-sensitive adhesive layer can be detachably anchored.

While the process according to the present invention has been described and illustrated on the basis of the disposable pants-type diaper 1 as the typical embodiment of the present invention, the present invention may be implemented as the process for making the other pants-type wearing article such as pants for incontinent patient or training pants. In such wearing article, configuration of the body fluid absorbent member 120 in the illustrated embodiments may be appropriately varied or the body fluid absorbent member 120 itself may be eliminated, depending on particular purpose for use of the article.

The present invention allows the disposable pants-type wearing article to be continuously made without the possibility that the shapes of the front and rear waist regions might become distorted and/or irregular.

What is claimed is:

1. A process of continuously making disposable wearing articles, said process comprising the steps of:
   continuously feeding, in a machine direction, a first web having opposite first and second surfaces, first and second side edges extending in parallel to each other in said machine direction, and a predetermined first width in a cross direction orthogonal to said machine direction;
   continuously feeding, in said machine direction, a second web having opposite third and fourth surfaces, a second width larger than the first width, third and fourth side edges extending in parallel to each other in said machine direction, wherein said third surface faces said first surface, said third and fourth side edges are adjacent said first and second side edges, respectively, and said first surface is placed upon and bonded to a middle zone of said third surface as viewed in said cross direction to form a composite web which is continuously fed in the machine direction;
   on said second surface of said first web or on said fourth surface of said second web in said composite web, forming a pair of first fasteners on both sides, as viewed in said machine direction, of a region to be formed with a cutting line so that said first fasteners are positioned between said first and second side edges and in a vicinity of said first side edge;
   between said region to be formed with said cutting line and respective said first fasteners, forming in said composite web a pair of slits extending in said cross direction beyond opposite ends of said first fasteners as viewed in said cross direction but without extending to said third and fourth side edges, wherein said slits are located on opposite sides, as viewed in said machine direction, of said region to be formed with said cutting line;
   attaching a fastener base sheet strip having a pair of second fasteners thereon to said composite web, wherein said fastener base sheet strip extends in said machine direction across said region to be formed with said cutting line and both said slits, and said second fasteners are detachably engaged with said first fasteners, respectively, on both sides of said region to be formed with said cutting line;
   forming in said composite web a notch extending from the third side edge to intersect both said slits;
   cutting away a section surrounded by at least said slits and said notch from said composite web and then folding portions of said second web located between said third and first side edges and between said fourth and second side edges along said first and second side edges, respectively, onto said second surface of said first web and bonding these portions to said second surface, wherein the cut away section is removed from beneath the fastener base sheet strip to form a gap between the pair of the first fasteners of the respective, successive diapers to be made along the first and third side edges, while maintaining the successive diapers in a connected state along the second and fourth side edges;
   subsequently to said step of folding of said portions, folding said composite web in said cross direction with said first and second side edges falling in line, wherein one of said second surface of said first web and said fourth surface of said second web, not provided with said first fasteners, lies inside;
   in a vicinity of said second side edge, bonding said composite web folded in two to said fastener base sheet strip in a bonding area of the region to be formed with said cutting line and between said slits; and
   subsequently to said bonding step, cutting said composite web together with said fastener base sheet strip along said cutting line, between said slits and through said bonding area.

2. The process as defined by claim 1, wherein
said first web comprises a first sub-web and a second sub-web extending in parallel in the machine direction without overlapping each other, said first sub-web having opposite first outer and inner side edges as viewed in said cross direction, said second sub-web having opposite second outer and inner side edges as viewed in said cross direction, said first outer side edge and said second outer side edge defining said first side edge and said second side edge of said first web, respectively, and said first inner side edge and said second inner side edge being spaced from each other in the cross direction; and
said second web overlaps both said first sub-web and said second sub-web, and said first and second inner side edges are connected with each other by said second web.

3. The process as defined by claim 1, further comprising the step of
attaching a body fluid absorbent member comprising an assembly of body fluid absorbent materials at least partially covered with a liquid-pervious sheet to said composite web.

4. The process as defined by claim 1, further comprising the step of
attaching a plurality of elastic members extending in said machine direction in a stretched state to and between said first web and said second web along said first side edge.

5. The process as defined by claim 1, wherein said second web is hydrophobic.

6. The process as defined by claim 1, wherein
prior to said bonding of said portions to the second surface, the fastener base sheet strip is free of direct bonding to the composite web and is detachably attached to the composite web via the first fasteners; and
after said bonding of said portions to the second surface, the fastener base sheet strip is directly bonded to the composite web in said bonding area.

7. The process as defined by claim 1, wherein the steps are performed in the recited order.

8. The process as defined by claim 1, wherein
the slits are formed across the first side edge while the third side edge is maintained intact until the notch is formed.

9. The process as defined by claim 1, further comprising
forming, in said web and along the cutting line to be form, a middle opening which defines leg holes of the disposable wearing articles to be made;
wherein
a peripheral edge of said middle opening intersects the slits to define, together with said slits and said notch, the cut-away section of said composite web.

10. The process as defined by claim 9, wherein said middle opening is formed before the notch.

11. The process as defined by claim 9, wherein said middle opening is formed before the step of bonding the fastener base sheet strip to the composite web.

12. The process as defined by claim 6, wherein the fastener base sheet strip is partially cut when said middle opening is formed.

13. The process as defined by claim 9, further comprising the step of
attaching a plurality of elastic members extending in said machine direction in a stretched state to and between said first web and said second web along said first side edge;
wherein
the step of cutting away the section of said composite web also severs said elastic members at a gap where the cut-away section used to be;
said gap extends continuously from the third side edge all the way to the peripheral edge of said middle opening; and
severed sections of the elastic members are restrained from contracting solely by the fastener base sheet strip which bridges the gap to thereby prevent distortion of the composite web along the first side edge due to the gap and tensile forces of the severed sections of the elastic members.

14. A process of continuously making disposable wearing articles, said process comprising the steps of:
continuously feeding, in a machine direction, a first web having opposite first and second surfaces, first and second side edges extending in parallel to each other in said machine direction, and a predetermined first width in a cross direction orthogonal to said machine direction;

continuously feeding, in said machine direction, a second web having opposite third and fourth surfaces, a second width larger than the first width, third and fourth side edges extending in parallel to each other in said machine direction, wherein said third surface faces said first surface, said third and fourth side edges are adjacent said first and second side edges, respectively, and said first surface is placed upon and bonded to a middle zone of said third surface as viewed in said cross direction to form a composite web which is continuously fed in the machine direction;

on said second surface of said first web or on said fourth surface of said second web in said composite web, forming a pair of first fasteners on both sides, as viewed in said machine direction, of a region to be formed with a cutting line so that said first fasteners are positioned between said first and second side edges and in a vicinity of said first side edge;

between said region to be formed with said cutting line and respective said first fasteners, forming in said composite web a pair of slits extending in said cross direction beyond opposite ends of said first fasteners as viewed in said cross direction but without extending to said third and fourth side edges, wherein said slits are located on opposite sides, as viewed in said machine direction, of said region to be formed with said cutting line;

attaching a fastener base sheet strip having a pair of second fasteners thereon to said composite web, wherein said fastener base sheet strip extends in said machine direction across said region to be formed with said cutting line and both said slits, and said second fasteners are detachably engaged with said first fasteners, respectively, on both sides of said region to be formed with said cutting line;

forming in said composite web a notch extending from the third side edge to intersect both said slits;

cutting away a section surrounded by at least said slits and said notch from said composite web and then folding portions of said second web located between said third and first side edges and between said fourth and second side edges along said first and second side edges, respectively, onto said second surface of said first web and bonding these portions to said second surface;

subsequently to said step of folding of said portions, folding said composite web in said cross direction with said first and second side edges falling in line, wherein one of said second surface of said first web and said fourth surface of said second web, not provided with said first fasteners, lies inside;

in a vicinity of said second side edge, bonding said composite web folded in two to said fastener base sheet strip in a bonding area of the region to be formed with said cutting line and between said slits;

subsequently to said bonding step, cutting said composite web together with said fastener base sheet strip along said cutting line, between said slits and through said bonding area;

forming, in said web and along the cutting line to be form, a middle opening which defines leg holes of the disposable wearing articles to be made;

wherein a peripheral edge of said middle opening intersects the slits to define, together with said slits and said notch, the cut-away section of said composite web; and attaching a plurality of elastic members extending in said machine direction in a stretched state to and between said first web and said second web along said first side edge;

wherein the step of cutting away the section of said composite web also severs said elastic members at a gap where the cut-away section used to be;

said gap extends continuously from the third side edge all the way to the peripheral edge of said middle opening; and severed sections of the elastic members are restrained from contracting solely by the fastener base sheet strip which bridges the gap to thereby prevent distortion of the composite web along the first side edge due to the gap and tensile forces of the severed sections of the elastic members.

* * * * *